United States Patent [19]

Carson

[11] Patent Number: 4,898,889
[45] Date of Patent: Feb. 6, 1990

[54] METHODS FOR THE TREATMENT OF HYPERTENSION

[75] Inventor: John R. Carson, Norristown, Pa.

[73] Assignee: McNeilab, Inc., Spring House, Pa.

[21] Appl. No.: 329,178

[22] Filed: Mar. 27, 1989

Related U.S. Application Data

[63] Continuation of Ser. No. 820,825, Jan. 21, 1986, abandoned, which is a continuation of Ser. No. 553,725, Nov. 21, 1983, abandoned.

[51] Int. Cl.⁴ .............. A61K 31/135; A61K 31/40; A61K 31/445; A61K 31/535
[52] U.S. Cl. .................. 514/654; 514/212; 514/227.5; 514/227.8; 514/231.5; 514/235.8; 514/236.2; 514/236.5; 514/236.8; 514/241; 514/247; 514/252; 514/255; 514/256; 514/317; 514/318; 514/326; 514/331; 514/343; 514/344; 514/345; 514/346; 514/351; 514/355; 514/357; 514/359; 514/362; 514/363; 514/365; 514/374; 514/396; 514/397; 514/406; 514/408; 514/422; 514/427; 514/428; 514/438; 514/445; 514/452; 514/464; 514/471; 514/524; 514/546; 514/552; 514/625; 514/629; 514/630; 514/333.8; 514/321; 564/374; 564/381; 564/382

[58] Field of Search .............. 514/212, 227.5, 227.8, 514/231.5, 235.8, 236.2, 236.5, 236.8, 255, 256, 317, 408, 428, 438, 524, 654, 241, 247, 318, 326, 331, 343, 344, 345, 346, 351, 355, 357, 359, 362, 363, 365, 374, 396, 397, 406, 422, 427, 445, 452, 464, 471, 546, 552, 625, 629, 630

[56] References Cited

U.S. PATENT DOCUMENTS 3,719,712  3/1973  Remy .................. 564/374
4,661,635  4/1987  Carson ................ 564/374
4,725,602  2/1988  Carson ................ 564/381

OTHER PUBLICATIONS

Remy et al., *J. Med. Chem.*, vol. 18, pp. 142–148 (1975).

*Primary Examiner*—Robert W. Ramsuer

[57] ABSTRACT

Acetylene compounds of the formula (I):

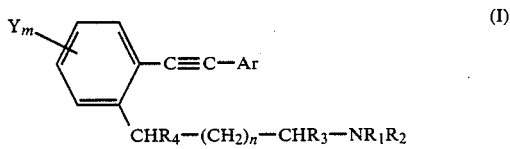

(I)

wherein Y, $R_1$, $R_2$, $R_3$, and $R_4$ are as described herein, m is 0–3, n is 0–2 and Ar is phenyl or an aromatic heterocycle are disclosed. The compounds possess antihypertensive and anti-anginal properties and may be used in the treatment of humans. Methods for the preparation and use of such acetylene compounds are also disclosed.

9 Claims, No Drawings

METHODS FOR THE TREATMENT OF HYPERTENSION

This is a continuation of application Ser. No. 820,825 filed Jan. 21, 1986 which is continuation of U.S. Ser. No. 553,725 filed Nov. 21, 1983 both abandoned.

This invention relates to a method for controlling hypertension and to a method for controlling the symptoms of angina pectoris by the administration of pharmaceutical compositions as well as compounds used in such methods.

Various phenylethynyl benzylamines are claimed in U.S. Pat. No. 3,719,712 and are taught as being useful as antiarrhythmic agents.

SUMMARY OF THE INVENTION

Acetylene compounds of the following formula (I):

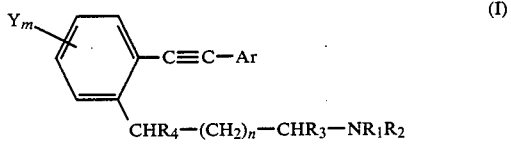

wherein Y, m, Ar, $R_1$, $R_2$, $R_3$, $R_4$ and n are as defined herein are useful in the treatment of hypertension and angina pectoris in mammals, e.g., in humans. Also part of the present invention is a method of treatment with the compounds of the invention, e.g., in the form of a pharmaceutical preparation for oral or parenteral administration.

DETAILED DESCRIPTION OF THE INVENTION

The present invention comprises compounds of the following formula (I):

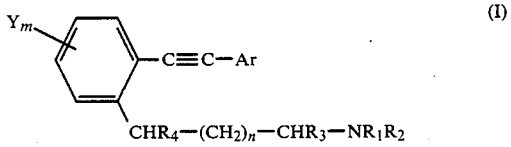

wherein
Y is independently alkyl, alkoxy, alkylthio, alkylsulfinyl, alkylsulfonyl, alkanoyloxy, alkanoylamino, amino, monoalkylamino, dialkylamino, hydroxy, halogen or cyano or methylenedioxy or ethylenedioxy at adjacent ring carbons;
m is 0, 1, 2 and 3;
Ar is phenyl or a 5- or 6-membered heterocyclic aromatic ring attached via a ring carbon to the acetylene moiety, which rings may be substituted independently by one or more of alkyl, alkoxy, alkylthio, alkylsulfinyl, alkylsulfonyl, carboxamido, halogen, fluoroalkyl or cyano;
$R_1$ and $R_2$ are independently hydrogen, alkyl, cycloalkyl or cycloalkylaklyl or $R_1$ and $R_2$ are alkyl and are joined to form a 5- to 7-membered saturated ring which ring may contain an oxygen or sulphur atom or an $NR_5$ moiety wherein $R_5$ is hydrogen, or alkyl;
$R_3$ is hydrogen, alkyl or alkoxyalkyl;
$R_4$ is hydrogen or alkyl; and
n is 0, 1 or 2, and the pharmaceutically acceptable acid addition salts and the quaternary ammonium compounds thereof.

In particular, Y is alkyl of about 1 to 6 carbons such as methyl or ethyl; alkoxy of about 1 to 6 carbon atoms such as methoxy or ethoxy; alkylthio of about 1 to 6 carbons such as methylthio, alkylsulfinyl of about 1 to 6 carbons such as methylsulfinyl; alkylsulfonyl of about 1 to 6 carbons such as methylsulfonyl; alkanoyloxy of about 2 to 6 carbons such as acetoxy; alkanoylamino of about 2 to 6 carbons such as acetylamino; amino; monoalkylamino of about 1 to 6 carbons such as ethylamino; dialkylamino of about 2 to 12 carbons such as dimethylamino; hydroxy; halogen such as fluoro, chloro or bromo, cyano; or methylenedioxy or ethylenedioxy wherein the two oxygen atoms are attached to two adjacent carbons of the benzene ring. Although the Y groups may be attached at any of the 4 open positions of the benzene ring, particularly preferred are compounds wherein the Y groups are attached at the 4- and/or 5-positions of the ring relative to the amino sidechain with the acetylene moiety being at the 2-position.

Ar is phenyl or a 5- or 6-membered heterocyclic aromatic ring containing 1, 2 or 3 heteroatoms such as nitrogen, sulphur or oxygen with specific examples being thiophene, pyrrole, furan, pyrazole, imidazole, triazole, oxazole, thiazole, thiadiazole, pyridine, pyridazine, pyrimidine, pyrazine or triazine. Such heterocycles may be attached via a ring carbon atom to the acetylene moiety. The optional substitution on the Ar ring is one or more, same or different, of alkyl, alkoxy or alkylthio of about 1 to 6 carbons, such as methyl, ethyl, methoxy, iso-propoxy or methylthio; alkylsulfinyl or alkylsulfonyl of about 1 to 6 carbons such as methylsulfinyl; carboxamido of the formula $-CONH_2$; halogen such as fluoro, chloro, bromo or iodo; fluroalkyl of about 1 to 6 carbons and one or more fluoro atoms with examples being 2,2,2-trifluoroethyl and trifluoromethyl; or cyano. Such optional substituents may be attached at any available site on the phenyl or heterocyclic ring, in particular at the meta and para positions of a phenyl ring relative to the acetylene.

$R_1$ and $R_2$ are the same or different and are hydrogen; straight or branched chain alkyl of about 1 to 8 carbons such as methyl ethyl, n-propyl, iso-propyl, tert-butyl, n-butyl or n-hexyl; cycloalkyl of about 3 to 6 carbons such as cyclopropyl or cyclohexyl; or cycloalkylalkyl of about 4 to 7 carbons such as cyclopropylmethyl; or $R_1$ and $R_2$ are alkyl groups and are joined to form a 5-, 6- or 7-membered saturated ring which may contain an additional heteroatom such as oxygen, sulphur or an $NR_5$ moiety wherein $R_5$ is hydrogen or alkyl of about 1 to 6 carbons, examples of rings from $R_1$ and $R_2$ being 1-pyrrolidinyl, 1-piperazinyl, 4-alkyl-1-piperazinyl, e.g., 4-methyl-1-piperazinyl, 1-morpholino, 1-thiamorpholino and 2-methyl-1-pyrrolindinyl.

$R_3$ is hydrogen; alkyl of about 1 to 6 carbons such as methyl, ethyl and iso-propyl; or alkoxyalkyl of about 1 to 6 carbons in each alkyl portion such as methoxymethyl, n-butoxymethyl and ethoxyethyl.

$R_4$ is in particular, hydrogen; or alkyl or about 1 to 6 carbons with examples being methyl, ethyl and n-butyl.

The pharmaceutically acceptable acid-addition salts of the compounds of formula (I) include those of a mineral or organic acid such as hydrochloric, hydrobromic, hydroiodic, sulfuric, phosphoric, fumaric, maleic, cyclohexylsulfamic, citric, lactic, methanesulfonic and similar acids.

The quarternary ammonium compounds of the compounds of formula (I) include those formed with an alkylhalide or sulfate of about 1 to 6 carbons, e.g., an alkyl bromide or iodide such as methyl iodide.

The salts may be prepared by reacting the free base in solution with an organic solvent with the desired acid and recovering the salt, usually as a precipitate from an organic solvent. The quarternary ammonium compounds may be prepared in an analogous manner using the desired alkyl halide or sulfate in place of an acid as known in the art.

Compounds of formula (I) and other compounds of the invention may exist in various isomeric forms, e.g., in view of the presence of an asymmetric carbon. It is understood that the present invention includes all such individual isomers and their racemates. Also within the scope of the invention are compounds of the invention in the form of hydrates and other solvate forms.

Particular compounds of the invention may be defined as those of formula (I) with one or more of the following definitions: Y is alkoxy; m is 1, 2 or 3 and the Y groups are at the 4, 5, 4 and 5, 3 and 5 or 3, 4 and 5 positions of the ring with the aminoalkyl and the acetylene moieties being at the 1 and 2 positions, respectively; $R_1$ and $R_2$ are joined to form a pyrrolidine ring or a piperazine ring; $R_3$ is alkyl or alkoxyalkyl; $R_4$ is alkyl; and at least one of $R_3$ and $R_4$ is other than hydrogen. Preferred moieties at particular positions are as follows: m is 1 and Y is methoxy; $R_1$ and $R_2$ are alkyl; and $R_3$ is alkyl.

An example of a preferred compound is that wherein Y is methoxy para to the acetylene, i.e., at the 5-position; m is 1; Ar is phenyl; $R_4$ is H; n is 0; $R_3$ is methyl; $R_1$ is methyl; and $R_2$ is n-hexyl.

Unless otherwise noted, "alkyl" in the present specification, e.g., as part of an alkoxy group, is indicative of a straight or branched chain group.

The compounds useful in the present invention may be made according to the following reaction scheme:

General Reaction Scheme

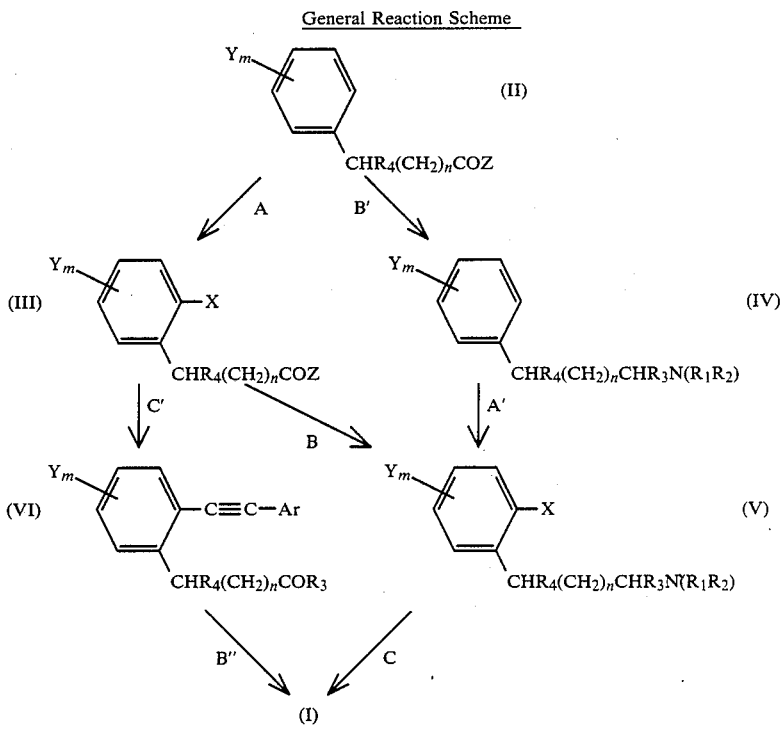

Three primary stages are used in the preparation of compounds of formula (I) by starting with arylalkanoic acids or aldehydes, arylalkanones or esters of the formula (II) wherein Z is OH, O alkyl, or $R_3$, e.g., hydrogen, alkyl or alkoxyalkyl. The stages are halogenation, construction of an amine functionality and condensation with an Ar-acetylene. In the halogenation, wherein X is Br or I, the aryl ring of (II) or (IV) is halogenated in the position ortho to the eventual aminoalkyl side chain, i.e., step A or A'. Brominations may be conducted using bromine in halocarbon solvents or acetic acid at temperatures from about $-20°$ to 80° C. and may be carried out in the presence of a Lewis acid catalyst such as ferric chloride. Iodinations may be carried out using iodine monochloride in halocarbon solvents or acetic acid over a range of room temperature of 100° C. Iodinations of arylalkylamines (IV) with iodine monochloride are preferably carried out in the presence of a strong acid such as methanesulfonic acid or hydrogen chloride. Iodinations may be carried out using iodine in the presence of an iodide scavenger such as silver acetate, silver sulfate, mercuric oxide or nitric acid. For reactive substrates, iodine may be used alone or in conjunction with a mild base such as sodium bicarbonate. Alternatively, the halogenation may be accomplished by mercuration, e.g., with $HgCl_2$ or thallation, e.g., with $Tl(O_2CCF_3)_3$, followed by treatment with iodide or bromide as described by A. McKillop et al in J. Am. Chem. Soc., 93, 4841 (1971).

In stage B or B', if $R_3$ is to be hydrogen in formula (I) an arylalkanoic acid of formula (II) or (III) where Z is OH may be converted to the corresponding acid chloride by reagents such as oxalyl chloride, thionyl chloride or phosphoryl chloride. The reaction may be carried out at room temperature to about 100° C. in an aprotic, nonpolar solvent such as toluene, chloroform or methylene chloride or the reaction may be carried out neat. The preferred method employs oxalyl chloride in toluene in the presence of DMF. The acid chloride is converted to the corresponding amide of formula (II) or (III) wherein Z is $NR_1R_2$. This conversion may be carried out by treatment of the acid chloride with an excess of amine of the formula $R_1R_2NH$, for instance in toluene or water at temperatures from −30° C. to 45° C. Alternatively, slightly more than one equivalent of amine may be used in the presence of an auxillary base such as triethylamine, pyridine, sodium hydroxide or potassium carbonate. The amides are then reduced to the corresponding amines of formulas (IV) and (V) wherein $R_3$ is hydrogen to complete the elaboration of the amine function. The reduction of the amides is preferably carried out with an excess of borane in THF at the reflux temperature of the solvent. The excess borane is decomposed by addition of water and the amine borane complex is decomposed by heating in the presence of an alkanoic acid, preferably propionic acid, a mineral acid or an alkali metal hydroxide to give the amines of formula (IV) or (V) wherein $R_3$ is hydrogen. Alternatively, the amides may be reduced with lithium aluminum hydride, sodium borohydride plus aluminum chloride or sodium borohydride in acetic acid or trifluoroacetic acid. A second method for construction of the amine function consists of reductive alkylation by aldehydes or ketones of the formula (II) or (III) wherein Z is $R_3$, i.e., H, alkyl or alkyloxyalkyl, of amines of the formula $R_1R_2NH$. The reductive alkylation may be carried out in one step from the carbonyl compound and the amine using sodium cyanoborohydride as the reducing agent in a lower alkanol or acetonitrile as the solvent at neutral to mildly acidic pH at temperatures from 0° to 40° C. Hydrogen over a noble metal or nickel catalyst may also be used to bring about the reduction. Reductive alkylation may also be carried out in two steps. The carbonyl compound and amine are first reacted to form an imine or iminium salt by treatment with molecular sieves or azeotropic removal of water. Reduction is then effected by sodium cyanoborohydride or catalytic reduction. Using the two step reductive alkylation, the alkyl groups $R_1$ and $R_2$ may be attached sequentially. A primary amine of formula (IV) or (V) wherein $R_1$ and $R_2$ are hydrogen may first be prepared by reductive alkylation of ammonia or an ammonium salt. Introduction of alkyl, cycloalkyl or cycloalkylalkyl as $R_1$ and $R_2$ may then be accomplished by reductive alkylation as described above using the appropriate carbonyl compounds and reducing agents. If the group to be introduced is methyl the Eschweiler-Clark procedure using formaldehyde as the carbonyl compound and formic acid or sodium cyanoborohydride as the reducing agent is used.

A method for construction of amines of formula (IV) wherein $R_4$ is H, n is 0 and $R_1$ and $R_2$ are H consists of condensation of an aromatic aldehyde of formula (VII) with a nitroalkane of the formula $R_3CH_2NO_2$ to afford a nitroolefin (VIII) followed by reduction to the amine of formula (IV):

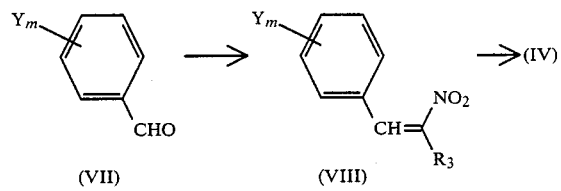

Condensation of the aldehyde with the nitroalkane is carried out using ammonium acetate or a primary alkyl amine as catalyst in, for example, glacial acetic acid, ethanol or toluene as a solvent at ambient to elevated temperatures, preferably at the reflux temperature of the solvent. Reduction of the nitroolefin may be accomplished using lithium aluminum hydride in an ether solvent, or by catalytic reduction over Raney nickel or a noble metal catalyst.

The third primary stage in the synthesis of compounds of formula (I) is labeled C and $C^1$ and is the replacement of halide X by an Ar-acetylene. This transformation may be accomplished by heating the aryl halide (V) with a cuprous Ar-acetylide at the reflux temperature of the solvent, preferably pyridine or DMF, as described by R. D. Stephens et al in J. Org. Chem., 28, 3313 (1963). Second, the coupling of arylhalide (V) with the Ar-acetylene may be accomplished by treating the arylhalide with chlorozinc Ar-acetylide in the presence of a palladium or nickel catalyst, preferably $Pd[(Ph_3)P]_4$ in an etherial solvent such as THF at −30° C. to ambient temperature, as described by A. O. King el al in J. Org. Chem., 43, 358 (1978). Third, the coupling may be accomplished by treating the arylhalide with the Ar-acetylene and catalytic quantities, e.g., 0.5 to 10 mole percent of $Pd(OAc)_2[P(Ph)_3]_2$ or $PdCl_2[P(Ph)_3]_2$ in an amine solvent such as diethylamine, piperidine, pyrrolidine or triethylamine at ambient temperature to the reflux temperature of the solvent in the presence or absence of cuprous iodide as described by K. Sonogashira, et al in Tetrahedron Lett. 4467 (1975) or H. A. Dieck et al in J. Organometal. Chem., 93, 253 (1975), respectively. When primary or secondary amines are sought the method of Stephens et al may not be used.

The primary stages may be carried out in the sequence A, B, C or the sequence B', A', C. The groups $R_1$ and $R_2$ when alkyl may be attached by reductive alkylation after carrying out stage C.

In addition, the halide of formula (III) where Z is a value of $R_3$ may be coupled with an Ar-acetylene in stage C' shown in the general reaction scheme under reaction conditions as described above for stage C. The product of the reaction is the acetylene of formula (VI) which may then be reacted in stage B'' under conditions described above for stages B and B' to construct the amine function to yield a compound of the formula (I). In B'', catalytic hydrogenation may not be employed in view of the possibility of hydrogenation of the acetylene moiety.

Starting materials for the general reaction scheme are widely known. However, starting materials with particular substituents may be synthesized by the following three methods:

First, alkanones of formula (II) wherein Z is $R_3$, n is 0 and $R_4$ is H may be prepared by condensation of an aromatic aldehyde (VII) with an alpha-haloester, e.g. of the formula $R_3CHBrCOOAlkyl$ in the presence of an alkali metal alkoxide to give a glycidic ester of the formula (IX). Hydrolysis with an alkali metal hydroxide followed by thermal decarboxylation affords the arylalkanone (II) wherein Z is $R_3$, n is 0 and $R_4$ is H. Conversion of such a (II) compound to one wherein $R_4$ is alkyl may be carried out by alkylation of an alkali metal enolate of the carbonyl compound (II) with a reagent such as ethyl iodide. Second, arylalkanones of formula (II) where Z is $R_3$, n is 1 and $R_4$ is H may be prepared by a Claisen-Schmidt condensation of a methyl ketone $CH_3COR_3$ with the aromatic aldehyde (VII) in the presence of an alkali metal hydroxide followed by hydrogenation of the alpha,beta-unsaturated ketone (X) over a noble metal catalyst. Third, arylalkanoic acids of the formula (II) wherein Z is OH, $R_4$ is H and n is 1 may be prepared by a Knovenagel condensation of the aromatic aldehyde (VII) with malonic acid followed by hydrogenation of the resulting cinnamic acid (XI) over a noble metal catalyst:

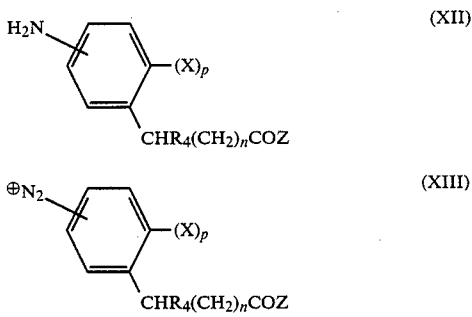

The various Y groups in compounds such as those of formulae (II), (III), (IV) and (XII) may be transformed among each other by techniques known in the art. For example, when Y is amino, the corresponding compound wherein Y is monoalkylamino may be prepared

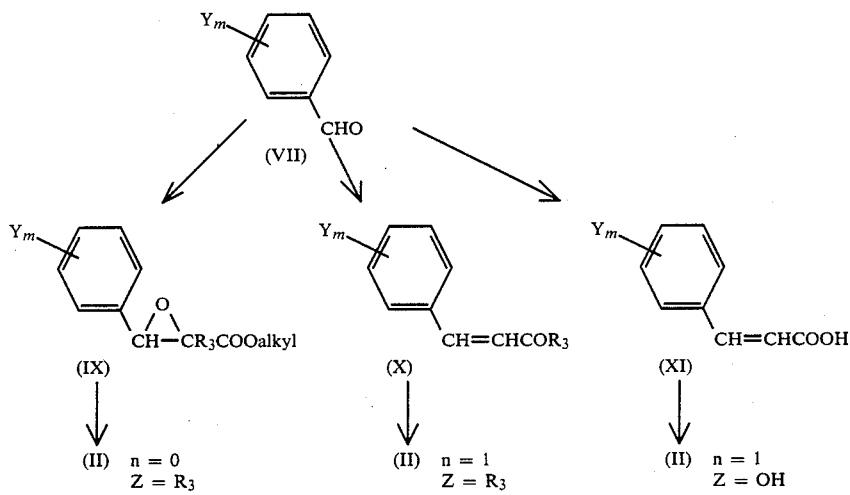

In each of the above three sequences, the aromatic aldehyde may be one with an X group ortho to the CHO and such a starting material will result in final products of the formula (III) after the steps described above.

For the preparation of intermediates (II) and (III) where Y is halo, alkylthio, hydroxy, cyano or dialkylamino, the corresponding compounds (XII) where p is 0 or 1, respectively, may be utilized as starting materials. The amine (XII) may be diazotized to give (XIII) and the diazonium group may be treated with CuCl, CuBr or CuCN to yield (II) or (III) wherein Y is Cl, Br or CN, respectively. Pyrolysis of the diazonium fluoroborate or hexafluoro phosphate gives the corresponding aryl fluoride. Hydrolysis of the diazonium salt would lead to the corresponding phenol. Treatment of the diazonium salt successively with potassium ethyl xanthate, base and an alkyl halide leads to the alkylthio product. Reductive alkylation of the amino compound (XII) with formaldehyde or an alkanal and sodium cyanoborohydride gives rise to intermediates (II) or (III) bearing the dialkylamino group.

by acylation with an acyl halide or anhydride to yield the corresponding compound where Y is alkanoylamino followed by hydride reduction with a borane or lithium aluminum hydride. When Y is alkylthio the corresponding compound where Y is alkylsulfinyl or alkylsulfonyl may be produced by oxidation with hydrogen peroxide or a peracid such as trifluoroperacetic acid as known in the art. Variation in the reaction temperature, reaction time and reactivity of the substrate and particular reagent will all be factors influencing whether the product is the sulfinyl or sulfonyl and manipulation of such variables is well known in the art. When Y is alkoxy, the corresponding compound wherein Y is hydroxy may be produced by conventional dealkylating reagents such as boron tribromide, boron trichloride, trimethylsilyliodide and hydrogen iodide. In addition, compounds wherein Y is alkoxy may be produced from the phenol by alkylation with a reagent such as alkyl halide, e.g., methyl iodide, in the presence of a base.

Ar-acetylenes as required may be prepared by the method of Ames et al as described in Synthesis, 364 (1981). Treatment of Ar iodides of the formula Ar-I with $PdCl_2[(Ph)_3P]_2$ or $Pd(OAc)_2[(Ph)_3P]_2$ and 2-methyl-3-butyn-2-ol affords acetylenic carbinols (XIV). Cleavage of the carbinol (XIV) with an alkali metal hydroxide gives rise to the Ar-acetylenes. The Ar-acetylenes may be converted to cuprous Ar-acetylides by treatment with cuprous iodide in ammonium hydroxide solution.

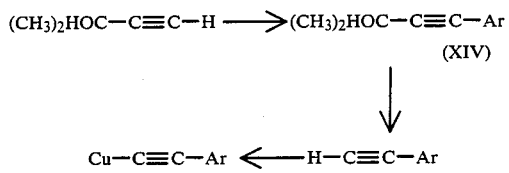

The compounds of formula (I) have been found to be useful for the treatment of hypertension. Their activity was determined using the spontaneously hypertensive rat (SHR) test as described below.

In this test, the arterial pressure of adult spontaneously hypertensive rats (Charles River) is monitored directly via an aortic cannula. The SHR rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages, allowed to recover from the anesthetic and are kept unrestrained. The arterial cannula is connected to the pressure transducer which is attached to the recorder. The test compounds are administered to at least 3 rats at a dose of 30 mg/kg by intraperitoneal (i.p.) injection. The arterial pressure and heart rate are monitored for a minimum of 24 hours. A test compound is considered to be active as an antihypertensive agent if the mean arterial pressure (MAP) indicates a fall of $>15$ mm of Hg. Each animal serves as its own control.

The results of this test for compounds of formula (I), expressed as "Mas Fall BP" (Maximum Fall in Mean Arterial Pressure) are shown in Table I.

In addition to their utility in the treatment of hypertension, the compounds of formula (I) are useful in the treatment of the symptoms of angina pectoris by virtue of their ability to dilate coronary arteries. Their activity was measured using the "Langendorff Isolated Heart" model. This test has been described in "Pharmacological Experiments on Isolated Preparations", Staff of the Department of Pharmacology, University of Edinbourgh, 2nd Ed., Churchill Livingstone, N.Y., 1970, pp. 112–119. The test compounds were administered at concentrations of 30, 10, 1, 0.1 and 0.03 micromolar $(10^{-6})$.

The minimum concentrate ($EC_{30}$) needed to elicit a 30 percent increase in coronary flow is shown in Table I for compounds of formula (I).

TABLE I

| Y | Ar | $R_1$ | $R_2$ | $R_3$ | $R_4$ | n | Max Fall BP(mmHg) | $EC_{30}$ $(10^{-6}$ M$)$ | Form[e] |
|---|---|---|---|---|---|---|---|---|---|
| 4,5-$CH_3O$ | $C_6H_5$ | $CH_3$ | $CH_3$ | H | H | 0 | 74 | 10 | FB |
| 4,5-$CH_3O$ | $C_6H_5$ | $CH_3$ | $CH_3$ | H | H | 1 | 67 | 3 | HCl |
| 5-$CH_3O$ | $C_6H_5$ | $CH_3$ | $CH_3$ | H | H | 0 | 91 | 1 | F |
| 4,5-$CH_3O$ | $C_6H_5$ | $CH_3$ | $CH_3$ | $CH_3$ | H | 0 | 84 | 10 | HCl |
| 4,5-$CH_3O$ | 4-$ClC_6H_4$ | $CH_3$ | $CH_3$ | H | H | 0 | 62 | 3 | F |
| H | $C_6H_5$ | $CH_3$ | $CH_3$ | H | H | 0 | 92 | 30 | F |
| 5-$CH_3O$ | 4$ClC_6H_4$ | $CH_3$ | $CH_3$ | H | H | 0 | 69 | 1 | F |
| 5-$CH_3O$ | $C_6H_5$ | $CH(CH_3)_2$ | $CH(CH_3)_2$ | H | H | 0 | 74 | 10 | F |
| 5-$CH_3O$ | $C_6H_5$ | $CH_3$ | $CH_3$ | $CH_3$ | H | 0 | 109 | 1 | HCl |
| 4,5-$CH_3O$ | $C_6H_5$ | —$(CH_2)_4$— | | H | H | 0 | 67 | 3.0 | F |
| 4,5-$CH_3O$ | $C_6H_5$ | $CH_3$ | H | H | H | 0 | 50 | 30 | HCl |
| 5-$CH_3O$ | $C_6H_5$ | $CH_3$ | $CH_3$ | H | H | 1 | 66 | 0.1 | F |
| 5-$CH_3O$ | 4-$CH_3OC_6H_4$ | $CH_3$ | $CH_3$ | H | H | 0 | 99 | 3.0 | F |
| 3,4,5-$CH_3O$ | $C_6H_5$ | $CH_3$ | $CH_3$ | $C_2H_5$ | $C_2H_5$ | 0 | 85 | 3.0 | F |
| 5-$CH_3O$ | 3-$CH_3C_6H_4$ | $CH_3$ | $CH_3$ | H | H | 0 | 91 | 3.0 | F |
| 5-$CH_3O$ | 3,5-$ClC_6H_3$ | $CH_3$ | $CH_3$ | H | H | 0 | 80 | 3.0 | F |
| 5-$CH_3O$ | $C_6H_5$ | —$C(CH_3)_3$ | H | H | H | 0 | 88 | 10 | HCl |
| 4,5-$CH_3O$ | 4-$CH_3OC_6H_4$ | $CH_3$ | $CH_3$ | H | H | 0 | 88 | 30 | M |
| 5-$CH_3O$ | 2-Thienyl | $CH_3$ | $CH_3$ | H | H | 0 | 92 | 1 | F |
| 5-$CH_3$ | $C_6H_5$ | n-$C_3H_7$ | n-$C_3H_7$ | H | H | 0 | 63 | 1 | HBr |
| 4,5-$(OCH_2O)$ | $C_6H_5$ | —$(CH_2)_4$— | | H | H | 1 | 62 | 10 | HCl |
| 4,5-$(OCH_2O)$ | $C_6H_5$ | $CH_3$ | $CH_3$ | H | H | 1 | 74 | 3 | F |
| 4,5-$CH_3O$ | $C_6H_5$ | —$(CH_2)_4$— | | H | H | 1 | 43 | 1 | HCl |
| 4,5-$CH_3O$ | $C_6H_5$ | —$(CH_2)_4$— | | $CH_3$ | H | 0 | 65 | 3 | F |
| 3,5-$CH_3O$ | $C_6H_5$ | $CH_3$ | $CH_3$ | H | H | 0 | (a) | 1.0 | F |
| 5-$CH_3O$ | $C_6H_5$ | $CH_3$ | $CH_3$ | $CH_3$ | H | 1 | (b) | 0.3 | P |
| 5-$CH_3O$ | $C_6H_5$ | $CH_3$ | n-$C_6H_{13}$ | H | H | 1 | 95 | 0.3 | P |
| 5-$CH_3O$ | $C_6H_5$ | H | H | $CH_3$ | H | 0 | (c) | 1.0 | HCl |
| 5-$CH_3O$ | $C_6H_5$ | $CH_3$ | n-$C_6H_{13}$ | $CH_3$ | H | 0 | (d) | 0.1 | F |

(a) max. fall BP at 100 mg/kg, p.o. = 38; not determined at 30 mg/kg, i.p.
(b) max. fall BP at 30 mg/kg, p.o. = 22; not determined at 30 mg/kg, i.p.
(c) max. fall BP at 100 mg/kg, p.o. = 78; not determined at 30 mg/kg, i.p.
(d) max. fall BP at 10 mg/kg, p.o. = 48; not determined at 30 mg/kg, i.p.
(e) F = fumarate
FB = free base
HCl = hydrochloride
M = maleate
HBr = Hydrobromide
P = Phosphate For the treatment of hypertension or angina, compounds of the present invention of the formula (I) may be administered orally or parenterally in a pharmaceutical composition comprising about 10 to 2,000 mg, preferably about 50 to 200 mg of one or more of the acetylene compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the acetylene compounds of the present invention of formula (I), an acid addition salt thereof or a quaternary ammonium compound thereof as the active ingredient may be prepared by intimately mixing the acetylene compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administraton and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

Also part of the present invention are novel intermediates, e.g., various compounds of the formulae (III), (IV), (V) and (VI), particularly (V) and (VI). In the following Examples, the following abbreviations are used: E (trans); Z (cis); bp (boiling point); mp (melting point); g (grams); ml (milliliters); glc (gas liquid chromatography); NMR (nuclear magnetic resonance): J (coupling constant); d (doublet); dd (double doublet); s (singlet); m (multiplet); t (triplet); N (normal); M (molar); THF (tetrahydrofuran); MeOH (methanol); DMF (dimethylformamide); mmoles (millimoles); mg (milligrams); mm (millimeters); and C,H,N. etc. (the chemical symbols for the elements). Unless otherwise indicated, all temperatures are reported in degrees centigrade (°C.), all pressures in mm of mercury, and NMR values in delta units.

EXAMPLE 1

2-Iodo-5-methoxybenzeneacetic Acid

A solution of 45 g (0.27 mole) of 3-methoxybenzeneacetic acid, 52.6 g (0.32 mole) of iodine monochloride and 1 g of iodine was allowed to stand in 500 ml of glacial acetic acid for six days at room temperature. The reaction was poured into water and the solid collected. It was recrystallized from toluene to give 51 g of crystalline 2-iodo-5-methoxybenzeneacetic acid, mp 133.5°–134.5° C. (65% yield).

EXAMPLE 2

Using the procedure of Example 1 and employing equivalent quantities of the following benzenealkanoic acids in place of 3-methoxybenzeneacetic acid, the following o-iodobenzenealkanoic acids were obtained respectively as products:

| Starting Acid | Product | % Yield | mp (°C.) |
| --- | --- | --- | --- |
| 3,4-Dimethoxybenzeneacetic Acid | 4,5-Dimethoxy-2-iodobenzeneacetic Acid | 82 | 165–7 |
| 3-Methoxybenzenepropanoic Acid | 2-Iodo-5-methoxybenzenepropanoic Acid | 69 | 98–101 |
| 3,4-Dimethoxybenzenepropanoic Acid | 4,5-Dimethoxy-2-iodobenzenepropanoic Acid | 88 | 149–151 |
| 3,4-Dimethoxybenzenepropanoic Acid | 3,5-Dimethoxy-2-iodobenzenepropanoic Acid | | |
| 1,3-benzodioxole-5-propanoic acid | 6-Iodo-1,3 benzodioxole-5-propanoic Acid | 66 | 143–5 |

EXAMPLE 3

Using the procedure of Example 1 and substituting the appropriate benzenealkanoic acid of formula (III) (Z=OH) for 3-methoxybenzeneacetic acid, the following o-iodobenzenealkanoic acids of formula (III) (Z=OH) may be prepared:

| Y | n |
| --- | --- |
| 3-CH$_3$O, 4-CH$_3$ | 0 |
| 3-C$_2$H$_5$O | 1 |
| 3-CH$_3$O | 2 |

EXAMPLE 4

2-Iodo-5-methoxybenzenepropanoic Acid

Samples of iodine (138.6 g, 0.759 mole) and silver acetate (126.7 g, 0.759 mole) were added in portions over 20 min. to a solution of 138.6 g (0.759 mole) of 3-methoxybenzenepropanoic acid in 750 ml glacial acetic acid. An additional 250 ml of glacial acetic acid was added. The mixture became warm and was stirred for one hour. The precipitated silver iodide was filtered and washed with acetic acid and the filtrate was poured into ice water and the solid collected. The solid was taken up in ether, washed with sodium thiosulfate solution and brine, dried with MgSO$_4$ and the solvent evaporated in vacuo. The residue was recrystallized from CHCl$_3$/ligroin to give 148.7 (64% yield) of 2-iodo-5-methoxybenzenepropanoic acid, mp 105°–106° C.

EXAMPLE 5

2-Iodo-5-methoxybenzeneacetic Acid

Using the procedure of Example 4 and employing an equivalent quantity of 3-methoxybenzeneacetic acid in place of 3-methoxybenzenepropanoic acid, there was obtained a 68% yield of 2-iodo-5-methoxybenzeneacetic acid, mp 132°–135° C.

EXAMPLE 6

1-[2-(4,5-Dimethoxy-2-iodophenyl)-1-methylethyl]pyrrolidine

A solution of 24.5 g (0.098 mole of 1-[2-(3,4-dimethoxyphenyl)-1-methylethyl]pyrrolidine, 17.5 g (0.1 mole) of iodine monochloride and 6.4 ml (0.098 mole) of methane sulfonic acid in 250 ml of glacial acetic acid was stirred at 25° for six days. An additional 4.5 g (0.028 mole) of iodine monochloride was added. After six days an additional 4.5 g of iodine monochloride was added. It was stirred for six days. The precipitated solid was collected by filtration. The solid was partitioned between ether and sodium hydroxide solution. The ether layer was washed with sodium thiosulfate solution, water and brine, dried with $K_2CO_3$ and concentrated to dryness in vacuo to give 21.7 g of a brown oil which crystallized. The material was recrystallized from acetonitrite to give 11.7 g (32% yield) of brown crystalline 1-[2-(4,5-dimethoxy-2-iodophenyl)-1-methylethyl]-pyrrolidine, mp 87°–88° C.

EXAMPLE 7

Using the procedure of Example 6 and employing equivalent quantities of the appropriate aralkylamine in place of 1-[2-(3,4-dimethoxyphenyl)-1-methylethyl]pyrrolidine, the following o-iodoaralkylamines of the formula (V) were obtained as products respectively.

| Starting Amine | Product | glc retention time, min[1] | mp °C. (salt) | % Yield |
|---|---|---|---|---|
| α,β-Diethyl-3,4,5-trimethoxy-N,N—dimethyl-benzene ethanamine | α,β-Diethyl-2-iodo-3,4,5-trimethoxy-N,N—dimethylbenzene-ethanamine | 6.13 | | 23 |
| 3-Methoxy-N,N,α-trimethylbenzeneethananamine | 2-Iodo-5-methoxy-N,N,α-trimethyl-benzeneethanamine | 5.05 | | 33 |
| 3,4-Dimethoxyphenyl-N,N,α-trimethylbenzeneethanamine | 2-Iodo-4,5-dimethoxyphenyl-N,N,α-trimethyl-benzeneethanamine | 5.53 | | 23 |
| 3-Methoxy-N,N,α-trimethylbenzenepropanamine | 2-Iodo-5-methoxy-N,N,α-trimethyl-benzenepropanamine | | 159–160 (HCl) | 52 |

[1]SE 30 Column, 90–280° C., 32°/min.

EXAMPLE 8

2-Iodo-5-methoxy-α-methylbenzeneethaneamine hydrochloride

Samples of iodine (49.7 g, 0.196 mole) and silver acetate (32.7 g, 0.196 mole) were added in portions to a solution of 29.4 g (0.178 mole) of 3-methoxy-α-methyl-benzeneethanamine in 473 ml of glacial acetic acid. The mixture was stirred for one hour. The acetic acid was evaporated in vacuo. The residue was partitioned between ether and sodium hydroxide solution. The ether layer was washed with water and brine and dried with $K_2CO_3$. The solvent was evaporated in vacuo to give 45.4 g of an oil. The hydrochloride was prepared from etherial hydrogen chloride and recrystallized from $CH_3CN$ to give 35.7 g of 2-iodo-5-methoxy-α-methyl-benzeneethanamine hydrochloride, mp 194°–196° C.

EXAMPLE 9

Using the procedure of Example 8 and substituting the appropriate starting materials of formula (IV) for 3-methoxy-α-methylbenzeneethanamine, the following products of formula (V) when X is iodo may be obtained as products:

| Y | $R_1, R_2$ | $R_3$ | $R_4$ | n |
|---|---|---|---|---|
| 3-$(CH_3)_2N$ | $CH_3$; $CH_3$ | $CH_3$ | H | 1 |
| 3-$CH_3O$ | $C_2H_5$; $C_2H_5$ | $n$-$C_3H_7$ | H | 1 |
| 3-$(CH_3)_2N$ | $CH_3$; $CH_3$ | $CH_3$ | H | 0 |
| 3-$CH_3O$ | $n$-$C_4H_9$; $CH_3$ | $CH_3$ | $CH_3$ | 0 |
| 3-$CH_3O$ | —$(CH_2)_5$— | $CH_3$ | $C_4H_9$ | 0 |
| 3-$CH_3O$ | $CH_3$; $CH_3$ | $CH_3OCH_2CH_2$ | H | 1 |
| 3-$CH_3O$ | $CH_3$; $CH_3$ | $n$-$C_5H_{11}$ | H | 0 |

EXAMPLE 10

1-(2-Iodo-5-methoxyphenyl)butane-3-one

Samples of iodine (42.4 g, 0.167 mole) and silver acetate (27.87 g, 0.167 mole) were added in portions to a solution of 29.8 g (0.167 mole) of 1-(3-methoxyphenyl)-butane-3-one in 167 ml of glacial acetic acid. The mixture was stirred one hour. The silver iodide was removed by filtration and washed with acetic acid. The filtrate was partitioned between ether and water. The ether layer was washed with water, sodium bicarbonate solution and sodium thiosulfate solution. The ether solution was dried with $MgSO_4$ and evaporated to dryness in vacuo. There was obtained 41.8 g (82% yield) of oily 1-(2-iodo-5-methoxyphenyl)butane-3-one.

$^1$HNMR (CDCl_3): 7.5–7.8 (d, J=9, 1H); 6.75–6.9 (d, J=3, 1H); 6.3–6.65 (dd, J=3, 10, 1H); 3.7–4.0 (s, 3H); 2.5–3.1 (m, 4H); 2.2 (s, 3H).

EXAMPLE 11

N,N-Dimethyl-2-iodo-5-methoxybenzeneacetamide

A 16.7 g (0.19 mole) sample of oxalyl chloride was added dropwise at 0° C. to a solution of 50.0 g (0.17 mole) of 2-iodo-5-methoxybenzeneacetic acid in 310 ml dry toluene and 31.7 ml of DMF. The mixture was allowed to warm to room temperature and stir for 16 hours. The solution was cooled to 0° C. and dimethylamine gas was admitted until the mixture was strongly basic. The mixture was allowed to warm to room temperature and stir for three hours and methylene chloride was added. The organic layer was washed with water, dilute hydrochloric acid, and sodium hydroxide. The organic layer was dried with $MgSO_4$ and evaporated in vacuo to give 54.2 g of N,N-dimethyl-2-iodo-5-methoxybenzeneacetamide, mp 86°–89° C.

Elemental Analysis: Calculated for $C_{11}H_{14}INO_2$: C, 41.39; H, 4.42; Found: C, 41.43; H, 4.45.

EXAMPLE 12

Using the procedure of Example 11 and employing equivalent quantities of the appropriate 2-iodobenzenealkanoic acid in place of 2-iodo-5-methoxybenzeneacetic acid and the appropriate amine ($R_1R_2NH$) in place of dimethylamine, the following 2-iodo-benzene alkanoic acid amides were obtained respectively:

| Product Amide | Yield % | mp° C. |
|---|---|---|
| 2-Iodo-5-methoxy N,N—dimethyl benzene propanamide | 74 | oil |
| N—Hexyl-2-iodo-5-methoxy-N—methylbenzenepropanamide | 93 | oil |
| 2-Iodo-5-methyl-N—methyl-benzenepropanamide | 89 | 118-19 |
| N—(1,1-Dimethylethyl)-2-iodo-5-methoxybenzeneacetamide | 45 | 111-13 |
| 2-Iodo-5-methoxy-N,N—dipropylbenzeneacetamide | 80 | oil |
| 1-[(2-Iodo-4,5-dimethoxyphenyl) | 45 | 134-6 |

-continued

| Product Amide | Yield % | mp° C. |
|---|---|---|
| acetyl]pyrrolidine | | |
| 2-Iodo-3,4-dimethoxy-N,N—bis-(1-methylethyl)benzeneacetamide | 78 | 143-7 |
| 2-Iodo-4,5-dimethoxy-N,N—dimethylbenzeneacetamide | 81 | 101-3 |
| 2-Iodo-4,5-dimethoxy-N,N—dimethylbenzenepropanamide | 80 | 86-8 |
| 1-[3-(2-Iodo-4,5-dimethoxyphenyl)-1-oxopropyl]pyrrolidine | 88 | 80-82 |
| 6-Iodo-N,N—dimethyl-1,3-benzodioxole-5-propanamide | 77 | 93-5 |
| 1-[3-(6-Iodo-1,3-benzodioxol-5-yl)-1-oxopropyl]-pyrrolidine | 88 | oil |
| 2-Iodo-3,5-dimethoxy-N,N—dimethylbenzenepropanamide | 80 | oil |
| 2-Iodo-N,N—dimethylbenzeneacetamide | 95 | oil |

EXAMPLE 13

Using the procedure of Example 11 and substituting the appropriate arylalkanoic acid of formula (III) (Z=OH) for 2-iodo-5-methoxybenzeneacetic acid and the appropriate amine ($R_1R_2NH$) for dimethylamine, the following amides of formula (III) (Z=$NR_1R_2$) wherein X is iodo may be obtained as products:

| Y | $R_1$ | $R_2$ | n |
|---|---|---|---|
| 3-CH$_3$O; 4-CH$_3$ | C$_2$H$_5$ | C$_2$H$_5$ | 0 |
| 3-C$_2$H$_5$O | n-C$_4$H$_9$ | n-C$_4$H$_9$ | 1 |
| 3-(CH$_3$)$_2$N | CH$_3$ | n-C$_6$H$_{13}$ | 1 |
| 3-CH$_3$S | CH$_3$ | CH$_3$ | 1 |
| 3-F | CH$_3$ | —CH$_2$CH(CH$_3$)$_2$ | 1 |
| 3-Cl | CH$_3$ | CH$_3$ | 1 |
| 3-CH$_3$O | —CH$_2$CH$_2$OCH$_2$CH$_2$— | | 0 |
| 3-CH$_3$O | —CH$_2$CH$_2$N(CH$_3$)—CH$_2$CH$_2$— | | 1 |
| 3-CH$_3$O | cyclohexyl | H | 1 |
| 3-CH$_3$O | CH$_3$ | CH$_3$ | 2 |

EXAMPLE 14

2-Iodo-5-methoxybenzenepropanoyl chloride

A mixture of 20 g (0.065 mole) of 2-iodo-5-methoxybenzenepropanoic acid and 14.3 ml (0.196 mole) thionyl chloride was heated at 65°-70° for three hours. The excess thionyl chloride was evaporated in vacuo to give 21 g (100% yield) of oily 2-iodo-5-methoxybenzenepropanoyl chloride.

EXAMPLE 15

2-Iodo-5-methoxy-N,N-dimethyl benzeneethanamine hydrochloride

A solution of 80.8 g (0.253 mole) of 2-iodo-5-methoxy-N,N-dimethylbenzeneacetamide in 800 ml of THF was added over ten minutes to 760 ml of 1M borane in THF. The mixture was heated under reflux for two hours. A 50 ml portion of water was added and the mixture stirred. The solvent was evaporated in vacuo and replaced with 200 ml of propionic acid. The mixture was heated for two hours and poured into ice-/sodium hydroxide solution and extracted with ether. The ether solution was washed with sodium hydroxide and water and dried with K$_2$CO$_3$. The ether was evaporated in vacuo to give 67.3 g of a clear oil which was distilled in a Kugelrohr at 125°-150° C. (0.17 Torr). The distillate was taken up in dilute hydrochloric acid and washed with ether. The aqueous layer was made basic with sodium hydroxide and extracted with ether. The ether solution was dried with K$_2$CO$_3$ and evaporated in vacuo to give 38.6 g (76% yield) of clear oily 2-iodo-5-methoxy-N,N-dimethylbenzeneethanamine. The hydrochloride was prepared from ether-hydrogen chloride, mp 167.5°-169° C.

EXAMPLE 16

Using the procedure of Example 15 and employing equivalent quantities of the appropriate amides from Example 12 in place of 2-iodo-5-methoxy-N,N-dimethylbenzeneacetamide, the corresponding amines were obtained as products, respectively:

| Product Amine | mp °C. (Salt) |
|---|---|
| 2-Iodo-5-methoxy-N,N—dimethylbenzenepropanamine | 168-170 (HCl) |
| N—Hexyl-2-iodo-5-methoxy-N—methyl-benzenepropanamine | 101-2 (tosylate) |
| 2-Iodo-5-methoxy-N—methylbenzenepropanamine | 127-8 (HClO$_4$) |
| 1-[3-(2-Iodo-4,5-dimethoxyphenyl)propyl]pyrrolidine | 177-8 (HCl) |
| N—(1,1-Dimethylethyl)-2-iodo-5-methoxybenzeneethanamine | 232-3 (HClO$_4$) |
| 2-Iodo-5-methoxy-N,N—dipropyl-benzeneethanamine | 126-7 (HCl) |
| 1-[(2-Iodo-4,5,dimethoxyphenyl)ethyl]pyrrolidine | 144-6 (HCl) |
| 2-Iodo-4,5-dimethyl-N,N—dimethyl-benzeneethanamine | 201-3 (HCl) |
| 2-Iodo-3,4-dimethoxy-N,N—bis-(1-methylethyl)benzeneethanamine | 191-3 (HCl) |
| 4-[(4-Chlorophenyl)(phenyl)methyl]-1[(2-iodo-4,5-dimethoxyphenyl)ethyl]piperazine | 120-148 (HCl) |
| 2-Iodo-4,5-dimethoxy-N,N—dimethyl-benzenepropanamine | 162-3 (HCl) |
| 6-Iodo-N,N—dimethyl-1,3-benzodioxole-5-propanamine | 135-7 (fumarate) |
| 2-Iodo-3,5-dimethoxy-N,N—dimethyl-benzenepropanamine | — |
| 2-Iodo-N,N—dimethylbenzeneethanamine | *55-77 (0.005 Torr) |
| 1-[3-(6-Iodo-1,3-benzodioxol-5-yl)propyl]pyrrolidine | 147-8 (hexamate) |

*boiling point (pressure)

EXAMPLE 17

Using the procedure of Example 15 and employing the appropriate amide of formula (III) (Z=$NR_1R_2$) in place of 2-iodo-5-methoxy-N,N-dimethylbenzeneacetamide the following products of formula (V) wherein X is iodo may be obtained as products:

| Y | $R_1$ | $R_2$ | n |
|---|---|---|---|
| 3-CH$_3$O; 4-CH$_3$ | C$_2$H$_5$ | C$_2$H$_5$ | 0 |
| 3-C$_2$H$_5$O | n-C$_4$H$_9$ | n-C$_4$H$_9$ | 1 |
| 3-(CH$_3$)$_2$N | CH$_3$ | n-C$_6$H$_{13}$ | 1 |
| 3-CH$_3$S | CH$_3$ | CH$_3$ | 1 |
| 3-F | CH$_3$ | —CH$_2$CH(CH$_3$)$_2$ | 1 |
| 3-Cl | CH$_3$ | CH$_3$ | 1 |
| 3-CH$_3$O | —CH$_2$CH$_2$OCH$_2$CH$_2$— | | 0 |
| 3-CH$_3$O | —CH$_2$CH$_2$N(CH$_3$)CH$_2$CH$_2$— | | 1 |
| 3-CH$_3$O | cyclohexyl | H | 1 |
| 3-CH$_3$O | CH$_3$ | CH$_3$ | 2 |

EXAMPLE 18

4-(3-Methoxyphenyl)-3-buten-2-one

A solution of 19.08 ml of 10% sodium hydroxide solution was added dropwise to a mixture of 103.6 g (0.761 mole) of 3-methoxybenzaldehyde, 117.2 g (2.02 mole) of acetone and 75 ml of water. The temperature was kept between 24° and 28° by intermittent application of cooling. After 2.75 hours the mixture was acidified with dilute hydrochloric acid and partitioned between $CH_2Cl_2$ and water. The organic layer was washed with water, dried with $MgSO_4$ and concentrated in vacuo to give 132.6 g of a yellow oil. The oil was distilled in a Kugelrohr at 0.5 Torr. A forerun bp 90°–110° C. was taken and discarded. The main fraction was taken between 110° and 120° C. There was obtained 91.68 g (68% yield) of 4-(3-methoxyphenyl)-3-buten-2-one as a yellowish oil.

EXAMPLE 19

4-(3-Methoxyphenyl)-2-butanone

A solution of 30.1 g of 4-(3-methoxyphenyl)-3-buten-2-one in 200 ml of MeOH was hydrogenated over 200 mg of 10% palladium on carbon for two hours. The catalyst was filtered and the solvent evaporated in vacuo to give 30.2 g of yellow oily 4-(3-methoxyphenyl)-2-butanone.

EXAMPLE 20

Using the procedures of Examples 18 and 19 and substituting the appropriate aryl aldehyde for 3-methoxybenzaldehyde and the appropriate method ketone for acetone, the following arylalkanones of formula (II) (n=1, Z=$R_3$, $R_4$=H) may be obtained as products:

| Y | $R_3$ |
|---|---|
| 3-$(CH_3)_2N$— | $CH_3$ |
| 3-$CH_3O$ | n-$C_3H_7$ |
| 3-$CH_3O$ | $CH_3OCH_2CH_2$ |

EXAMPLE 21

Ethyl 2-ethyl-3-(3,4,5-trimethoxyphenyl)oxiraneacetate

A mixture of 72.4 g (0.36 mole) of 3,4,5-trimethoxybenzaldehyde and 70.2 g (0.36 mole) of ethyl α-bromobutyrate in 200 ml of anhydrous ether was cooled to −5° C. and stirred under an atmosphere of nitrogen while adding 44.8 g (0.4 mole) of potassium t-butoxide portionwise over a three hour period. The mixture was allowed to warm to room temperature and stirring was continued overnight.

The mixture was treated with 200 ml of 1N hydrochloric acid, shaken, and the organic layer separated. The organics were washed sequentially with saturated solutions of sodium thiosulfate, sodium bicarbonate, and sodium chloride. The ether extract was dried over anhydrous magnesium sulfate and evaporated in vacuo to yield 75.5 g of ester product as an oil. Distillation at 151°–152° C. at 0.055 mm of Hg yielded 55.4 g (50%) of ethyl 2-ethyl-3-(3,4,5-trimethoxyphenyl)oxiraneacetate.

EXAMPLE 22

1-(3,4,5-Trimethoxyphenyl)-2-butanone

A solution of 50.4 g (0.162 mole) ethyl 2-ethyl-3-(3,4,5-trimethoxyphenyl)oxiraneacetate in 100 ml of 95% ethanol was added to 6.48 (0.162 mole) of sodium hydroxide in 95% ethanol. The mixture was heated under reflux for three hours under nitrogen. The solvent was evaporated in vacuo. The residue was dissolved in water and acidified with dilute hydrochloric acid. The mixture was extracted with ether and the ether layer was washed with brine, dried and the solvent evaporated in vacuo. The residue was heated at 155° under nitrogen for six hours and dissolved in ether, washed with sodium hydroxide and brine, dried with $MgSO_4$ and the solvent evaporated in vacuo to give 27.9 g of an oil. The oil was distilled at 117°–126° C. at 0.05 Torr to give 22.1 g (57.4% yield) of 1-(3,4,5-trimethoxyphenyl)-2-butanone as a yellow oil.

EXAMPLE 23

4-(3,4,5-Trimethoxyphenyl)-3-hexanone

Dry sodium methoxide was prepared by evaporating a solution of sodium methoxide, prepared from 4.27 g (0.186 mole) of sodium metal in 67 ml of anhydrous methanol, on a steam batch at aspirator pressure initially, and then for three hours at 200° C. at 0.02 mm.

The dried sodium methoxide was combined with 22.08 g (0.093 mole) of ethyl 3,4,5-trimethoxybenzyl ketone and flushed with nitrogen. The mixture was cooled and stirred while adding 43.3 g (0.279 mole) of ethyl iodide, allowed to warm to room temperature, and finally refluxed for one hour. The resulting residue was cooled and partitioned between water and ether. The aqueous layer was separated and extracted several times with additional ether. The combined ether extracts were washed with sodium thiosulfate solution, brine, and dried over anhydrous magnesium sulfate. Evaporation in vacuo yielded 22.6 of crude product as an oil. The oil was distilled and the fraction collected between 106°–110° C. at 0.025–0.05 mm to yield 19.58 g (80%) of 4-(3,4,5-trimethoxyphenyl)-3-hexanone.

EXAMPLE 24

Using the procedures of Examples 21, 22 and 23, substituting the appropriate aromatic aldehyde for 3,4,5-trimethoxybenzaldehyde, the appropriate α-haloester for ethyl α-bromobutyrate, and the appropriate alkyl halide for ethyl iodide the following arylalkanones of formula (II) (n=O, Z=$R_3$) may be prepared respectively:

| Y | $R_3$ | $R_4$ |
|---|---|---|
| 3-$(CH_3)_2N$ | $CH_3$ | H |
| 3-$CH_3O$ | $CH_3$ | $CH_3$ |
| 3-$CH_3O$ | n-$C_5H_{11}$ | H |

EXAMPLE 25

1-[2-(3,4-Dimethoxyphenyl)-1-1-methylethyl]pyrrolidine

A 53 ml (0.644 mole) portion of pyrrolidine was added to a solution of 25 g (0.129 mole) of 1-(3,4-dimethoxyphenyl)-2-propanone in 150 ml of methanol. A solution of 6.4 g of sodium cyanoborohydride (0.103 mole) in 50 ml of methanol was added. Enough 5N hydrogen chloride in methanol was added to bring the pH of the mixture to 6. The mixture was stirred two hours at 25°. Methanolic hydrogen chloride was added to bring the pH to 1. The mixture was allowed to stand for 16 hours. The methanol was evaporated in vacuo and the residue partitioned between sodium hydroxide solution and ether. The ether layer was washed with brine, dried with $MgSO_4$ and evaporated in vacuo to give 28 g of an orange oil which was distilled in a Kugelrohr at 115° (0.1 Torr) to give 24.5 g (76% yield) of 1-[2-(3,4-dimethoxyphenyl)-1-methylethyl]pyrrolidine as a colorless oil.

EXAMPLE 26

Using the procedure of Example 25 and employing equivalent quantities of the appropriate carbonyl compounds in place of 1-(3,4-dimethoxyphenyl)-2-propanone and the appropriate amine in place of pyrrolidine, the respective reductive alkylation products were obtained:

| Product Amine | % Yield | mp °C. (salt) | glc Retention Time a |
|---|---|---|---|
| 2-Iodo-5-methoxy-N—methylbenzene propanamine | 44 | 189-90 (HCl) | |
| 3-Methoxy-N,N,α-trimethylbenzeneethanamine | 85 | | 3.62 |
| 3,4-Dimethoxyphenyl-N,N, α-trimethylbenzene-ethanamine | 96 | | 4.73 |
| α,β-Diethyl-3,4,5 trimethoxy-N—methyl-benzeneethanamine | 51 | | | a SE 30 column, 90–280° C., 32°/min.

EXAMPLE 27

Using the procedure of Example 25 substituting the appropriate arylalkanone for 1-(3,4-dimethoxyphenyl)-2-propanone) and the appropriate amine for pyrrolidine the following aryl alkylamines of formula (IV) may be prepared:

| Y | $R_1$ | $R_2$ | $R_3$ | $R_4$ | n |
|---|---|---|---|---|---|
| 3-$(CH_3)_2N$ | $CH_3$ | $CH_3$ | $CH_3$ | H | 1 |
| 3-$CH_3O$ | $C_2H_5$ | $C_2H_5$ | n-$C_3H_7$ | H | 1 |
| 3-$(CH_3)_2N$ | $CH_3$ | $CH_3$ | $CH_3$ | H | 0 |
| 3-$CH_3O$ | n-$C_4H_9$ | $CH_3$ | $CH_3$ | $CH_3$ | 0 |
| 3-$CH_3O$ | —$CH_2CH_2CH_2CH_2CH_2$— | | $CH_3$ | $C_4H_9$ | 0 |
| 3-$CH_3O$ | $CH_3$ | $CH_3$ | $CH_3OCH_2CH_2$ | H | 1 |
| 3-$CH_3O$ | $CH_3$ | $CH_3$ | n-$C_5H_{11}$ | H | 0 |

EXAMPLE 28

α,β-Diethyl-3,4,5-trimethoxy-N,N-dimethylbenzeneethanamine

A solution of 35.4 g (0.126 mole) of α,β-diethyl-3,4,5-trimethoxy-N-methylbenzeneethanamine, 25.6 g (0.316 mole) formalin, 15 g (0.316 mole) formic acid in 350 ml DMF was heated under reflux for five hours. The mixture was partitioned between water and methylene chloride. The organic layer was dried with MgSO and evaporated in vacuo. The residue was warmed at 0.75 Torr for one hour. There was obtained 34 g (91% yield) of α,β-diethyl-3,4,5-trimethoxy-N,N dimethylbenzeneethanamine as an oil $^1H$ NMR (CHCl$_3$): 6.7 (s, 2H); 3.8 (s 9H); 2.7–2.2 (m, 2H); 2.2 (s, 6H); 2.0–1.2 (m, 4H); 0.9 (t, 3H); 0.7 (t, 3H).

EXAMPLE 29

1-Methoxy-3-(2-nitro-1-propenyl)benzene

A mixture of 71.9 g (0.528 mole) of m-anisaldehyde, 118.9 g (1.584 mole) of nitroethane, 40.7 g (0.528 mole) of ammonium acetate, and 350 ml of glacial acetic acid was heated to reflux for one hour. The mixture was then allowed to cool and partitioned between ether and water. The ether layer was separated and washed sequentially with water 3N sodium hydroxide, water and brine. The organic phase was dried over anhydrous magnesium sulfate and evaporated in vacuo to give the crude product. After a preliminary distillation at 125° C./0.0001 mm, the product was finally crystallized from absolute ethanol to yield the pure product, a yellow solid, mp 40°–42° C.

EXAMPLE 30

3-Methoxy-α-methylbenzeneethaneamine

Two separate 3 liter three-necked round bottom flasks were each equipped with an overhead stirrer, condenser, addition funnel and nitrogen inlet tube. The flasks were purged with nitrogen and charged with 19.64 g (0.517 mole) of lithium aluminum hydride and 60 ml of anhydrous ether. To each flask was slowly added a solution of 35 g (0.129 mole) of 1-methoxy-3-(2-nitro-1-propenyl)benzene in 150 ml of anhydrous ether. An additional 500 ml of anhydrous ether was added to each flask, and the mixture allowed to stir overnight. After cooling in an ice bath, each reaction was treated cautiously and sequentially with 20 ml of water, 20 ml of 3N sodium hydroxide, and 60 ml of water, while maintaining cooling and stirring in the ice bath. Cooling and stirring were continued for 30 minutes, after which time the batch was removed and stirring continued until the inorganics formed a white solid. The inorganics were removed by filtration and washed with ether. The combined ether filtrates were washed with dilute sodium hydroxide, water, and brine. The ether layer was dried over anhydrous potassium carbonate and filtered. The filtrate was treated with etheral hydrogen chloride to form the hydrochloride salt (mp 115°–118° C.) of the product, which was then converted back to yield 20.4 g of the free base, an oil.

EXAMPLE 31

1-(3,5-Dichlorophenyl)-3-methyl-1-butyn-3-ol

A mixture of 25.5 g (0.094 mole) of 3,5-dichloroiodobenzene, 550 ml dry triethylamine, 12 g (0.14 mole) of 2-methyl-2-hydroxy-3-butyne, 0.42 g (0.0019 mole) palladium (II) acetate, and 1 g (0.0038 mole) of triphenylphosphine was heated to reflux under nitrogen for four hours. The resulting mixture was cooled, diluted with ether and washed with two 500-ml portions of 3N hydrochloric acid. The ether layer was separated, dried over anhydrous magnesium sulfate, and evaporated in vacuo to yield the crude product as an oily residue. The purified product was obtained by distillation to yield 7.95 g, bp 115°–125° C./0.0001 mm.

EXAMPLE 32

1,3-Dichloro-5-ethynylbenzene

A mixture of 7.95 g (0.0655 mole) of 1-(3,5-dichlorophenyl)-3-methyl-1-butyn-3-ol and 30 g of sodium hydroxide in 150 ml of dry toluene was heated to reflux with stirring for 3.5 hours. The toluene was removed in vacuo to yield a brown solid residue. The residue was triturated with hexane and the resulting hexane solution washed with aqueous sodium thiosulfate solution. The hexane layer was separated and evaporated in vacuo to yield the crude product. Recrystallization from hexane yielded 4.15 g of pure product, mp 80°–81.5° C.

EXAMPLE 33

Copper I (3,5-Dichlorophenyl)acetylide

A mixture of 77 g of copper (II) sulfate pentahydrate and 30 ml of concentrated ammonium hydroxide was stirred under an atmosphere of nitrogen and 125 ml of water added. Stirring was continued until all of the copper sulfate dissolved, then 43 g of hydroxylamine hydrochloride was added with continued stirring for 30 minutes to form a pale blue solution. A solution of 4.15 g of 1,3-dichloro-5-ethynylbenzene in 150 ml of absolute ethanol was added dropwise with stirring to the pale blue copper solution. Stirring was continued an additional two hours, the mixture filtered and the resulting bright yellow product, a solid, washed sequentially with water, ethanol, and ether. The product was dried in vacuo to yield 4.25 g of copper (I) (3,5-dichlorophenyl)acetylide.

EXAMPLE 34

Using the procedures of Examples 31 and 32 substituting the appropriate Ar-iodide for 3,5-dichloroiodobenzene the following Ar-acetylenes were prepared respectively:

| Ar-iodide | Ar-acetylene | % Yield | bp (20 mm/Hg) |
|---|---|---|---|
| 3-Iodotoluene | 3-Methylphenylacetylene | 88 | 90–110° |
| 4-Iodoanisole | 4-Methoxyphenylacetylene | 45 | 90° |
| 2-Iodothiophene | 2-Ethynylthiophene | 54 | 90–110° |

EXAMPLE 35

Using the procedures of Examples 31 and 32 and substituting the appropriate aryl iodide for 3,5-dichloroiodobenzene the following Ar-acetylenes may be obtained:
Ar=o-$CF_3C_6H_4$; p-NC-$C_6H_4$; p-$CH_3SC_6H_4$; 2,3-$(CH_3O)_2C_6H_3$; 4-Cl, 3$CH_3C_6H_3$, 2-pyridyl.

EXAMPLE 36

Using the procedure of Example 33 and employing equivalent quantities of the Ar-acetylenes from Example 34 in place of 1,3-dichloro-5-ethynylbenzene the following copper (I) Ar-acetylides were obtained as bright yellow amorphous powders respectively:

| Ar-acetylene | Cu (I) Ar-acetylide | % Yield |
|---|---|---|
| 3-Methylphenyl-acetylene | Cu (I) 3-Methylphenyl-acetylide | 32 |
| 4-Methoxyphenyl-acetylene | Cu (I) 4-methoxyphenyl-acetylide | 70 |
| 2-Ethynylthiophene | Cu (I) 2-thienylacetylide | 9 |
| 4-Chlorophenyl-acetylene | Cu (I) 4-Chlorophenyl-acetylide | 88 |

EXAMPLE 37

5-Methoxy-N,N-dimethyl-2-(phenylethynyl)benzeneethanamine Hydrochloride

A mixture of 15.0 g (0.049 mole) of 2-iodo-5-methoxy-N,N-dimethylbenzeneethanamine and 12.1 g (0.074 mole) of copper (I) phenylacetylide in 150 ml of dry pyridine was heated under reflux under nitrogen for 18 hours. The pyridine was evaporated in vacuo. The residue was triturated with ammonium hydroxide solution and ether. The ether layer was washed with brine, dried and evaporated in vacuo to an oil. The hydrochloride was prepared from ether-hydrogen chloride and recrystallized successively from 2-propanol and absolute ethanol. There was obtained 6.9 g (44% yield) of white crystalline 5-methoxy-N,N-dimethyl-2-(phenylethynyl)benzeneethanamine hydrochloride, mp 190°–191° C.

Elemental Analysis: Calculated for $C_{19}H_{21}NO.HCl$: C, 72.25; H, 7.06; Found: C, 71.94; H, 7.01.

EXAMPLE 38

Using the procedure of Example 37 and substituting equivalent quantities of the appropriate iodoamine (from Examples 15, 16 and 6) for 2-iodo-5-methyl-N,N-dimethylbenzeneethanamine and the appropriate copper (I) Ar-acetylide (from Example 36) for copper (I) phenylacetylide, the following products were obtained:

| Compound of Formula (I) | mp | % Yield |
|---|---|---|
| 5-Methoxy-N,N—dimethyl-2-(phenylethynyl)benzene-propanamine (E)-2-Butenedioate (1:1) | 128.5–129.5 | 30 |
| 5-Methoxy-N,N—dimethyl-2-(2-thienylethynyl)benzeneethanamine (E)-2-Butenedioate (1:1) | 160–163 | 16 |
| 2-(3,5-Dichlorophenylethynyl)-5-methoxy-N,N—dimethylbenzene-ethanamine (E)-2-Butenedioate (1:1) | 188–189 | 45 |
| 5-Methoxy-N,N—dimethyl-2[(3-methylphenyl)ethynyl]benzene-ethanamine (E)-2-butenedioate (1:1) | 140–142 | 35 |
| 2-[(4-Methoxyphenyl)ethynyl]-5-methoxy-N,N—dimethylbenzene-ethanamine (E)-2-Butenedioate (1:1) | 165–166 | 18 |
| 2-[(4-Chlorophenyl)ethynyl]-5-methoxy-N,N—dimethylbenzene-ethanamine (E)-2-Butenedioate (1:1) | 178–179 | 58 |
| N,N—Dimethyl-2-(phenylethynyl)benzeneethanamine (E)-2-Butenedioate (1:1) | 144–145 | 23 |
| 1-(3-[4,5-Dimethoxy-2-(phenylethynyl)phenyl]propyl)pyrrolidine hydrochloride | 183-5 | 85 |
| 1-(2-[4,5-Dimethoxy-2-(phenylethynyl)phenyl]-1-methylethyl)pyrrolidine (E)-2-butendioate (2:1) | 135–138 | 36 |
| 3,5-Dimethoxy-N,N—dimethyl-2-(phenylethynyl)benzenepropanamine (E)-2-butenedioate (1:1) | 131–133 | — |
| N,N—Dimethyl-6-(phenylethynyl)-1,3-benzodioxole-5-propanamine (E)-2-butenedioate (1:1) | 123–125 | 60 |
| 1-(3-[6-(Phenylethynyl)-1,3-benzodioxol-5-yl]propyl)pyrrolidine hydrochloride | 202–204 | 52 |
| α,β-Diethyl-3,4,5-trimethoxy-N,N—dimethyl-2-(phenyethynyl)benzeneethanamamine (E)-2-butenedioate (1:1) | 166–168 | 23 |
| 4,5-Dimethoxy-N,N—bis(1-methylethyl)-2-(phenylethynyl)benzeneethanamine (E)-2-butenedioate (1:1) | 185–187 | 53 |
| 1-(2-[4,5-Dimethoxy-2-(phenylethynyl)phenyl]ethyl)pyrrolidine (E)-2-butenedioate (1:1) | 173–175 | 64 |
| 5-Methoxy-N,N,α-trimethyl-2-(phenylethynyl)benzeneethanamine (E)-2-butenedioate (1:1) | 206–208 | 65 |
| 4,5-Dimethoxy-N,N,α60 -trimethyl-2-(phenylethynyl)benzeneethanamine (E)-2-butenedioate (1:1) | 183–185 | 49 |
| 4,5-Dimethoxy-N,N—dimethyl-2-(phenylethynyl)benzenepropanamine hydrochloride | 178–180 | 47 |
| 4,5-Dimethoxy-N,N—dimethyl-2-(phenylethynyl)benzeneethamine | 67–69 | 62 |
| 2-(4-Chlorophenylethynyl)-4,5-dimethoxy-N,N—dimethylbenzene-ethanamine hydrochloride | 200–201 | 35 |
| 4,5-Dimethoxy-2-(4-methoxyphenyl-ethynyl)-N,N—dimethylbenzene- | 153-5 | 35 |

| Compound of Formula (I) | mp | % Yield |
|---|---|---|
| ethanamine (Z)-2-Butenedioate (2:1) | | 5 |

EXAMPLE 39

5-Methoxy-N,N,α-trimethyl-2-(phenylethynyl)benzenepropanamine (E)-2-butendioate hydrate (16:16:1)

A solution of 18.87 ml (0.03 mole) of 1.6M n-butyllithium in hexane was added to 3.38 ml (0.03 mole) of phenyl acetylene in 40 ml of dry THF at 0° under argon. The solution was stirred for 15 minutes at 0° and transferred via cannula to a flask containing 4.12 g (0.03 mole) of freshly dried $ZnCl_2$ under argon. The mixture was stirred for 20 minutes at 0°. A solution of 8.41 g (0.025 mole) of 2-iodo-5-methoxy-N,N,α-trimethylbenzenepropanamine and 0.58 g (0.5 mmole), 2mole % of tetrakis triphenylphosphine palladium (O) in 100 ml dry THF was added via cannula. The mixture was allowed to warm to 25° and was stirred for 18 hours. A 20 ml sample of water was added and the mixture stirred for 20 minutes. The mixture was partitioned between water and methylene chloride. The methylene chloride solution was washed with dilute hydrochloric acid and dilute sodium hydroxide solution, dried with $K_2CO_3$ and evaporated in vacuo. The oil was taken up in MeOH and a solid removed by filtration. The methanol was evaporated in vacuo and the residue was taken up in ether, filtered and evaporated to dryness. A fumarate (1:1) was prepared out of methanol. It was recrystallized successively from acetonitrile and 2-propanol. There was obtained 6.48 g (67% yield) of white crystalline 5-methoxy-N,N,α-trimethyl-2-(phenylethynyl)benzenepropanamine (E)-2-butendioate hydrate (16:16:1), mp 146°–148° C.

Elemental Analysis: Calculated for $C_{21}H_{25}NO·C_4H_4O·1/16 H_2O$: C, 70.71; H, 6.9; N, 3.30; $H_2O$, 0.26. Found: C, 70.99; H, 6.96; N, 3.25; $H_2O$, 0.26.

EXAMPLE 40

Using the procedure of Example 39 and substituting equivalent quantities of the appropriate iodoamines for 2-iodo-5-methoxy-N,N,α-trimethylbenzenepropanamine there were obtained as products respectively:

| Compound of Formula (I) | mp (°C.) |
|---|---|
| 5-Methoxy-N,α-dimethyl-2-(phenylethynyl)benzene propanamine hydrochloride | 126–128 |
| N—Hexyl-5-methoxy-N—methyl-2-(phenylethynyl) benzenepropanamine phosphate hydrate (4:5:2) | 84–88 |
| N—(1,1-Dimethylethyl)-5-methoxy-2-(phenylethynyl) benzeneethanamine hydrochloride | 248–250 |
| 5-Methoxy-2-(phenylethynyl)-N,N—dipropyl benzeneethanamine hydrobromide | 143–145 |
| 5-Methoxy-α-methyl-2-(phenylethynyl) benzeneethanamine hydrochloride | 209–211 |

EXAMPLE 41

5-methoxy-N,N-dimethyl-2-(phenylethynyl)benzeneethanamine

To a solution of 1 g (3.3 mmoles) of 2-iodo-5-methoxy-N,N-dimethylbenzeneethanamine and 0.33 g (3.3 mmoles) phenylacetylene in 18 ml dry triethylamine were added, under nitrogen, 23.1 mg bis(triphenylphosphine) palladium (II) chloride and 11.4 mg Copper (I) iodide. The reaction mixture was stirred overnight. The yield by glc using internal standard of 5-methoxy-N,N-dimethyl-2-(phenylethynyl)benzeneethanamine was 91%.

EXAMPLE 42

Using the procedure of Example 39 and substituting the appropriate starting materials of the formula (V) and an Ar-acetylene for 2-iodo-5-methoxy-N,N, α-trimethylbenzenepropanamine and phenylacetylene respectively, the following products of formula (I) may be obtained:

| Y | Ar | $R_1$ | $R_2$ | $R_3$ | $R_4$ | n |
|---|---|---|---|---|---|---|
| 5-$(CH_3)_2$N | o-$CF_3C_6H_4$ | $CH_3$ | $CH_3$ | $CH_3$ | H | 1 |
| 5-$CH_3$O | $C_6H_5$ | $C_2H_5$ | $C_2H_5$ | n-$C_3H_7$ | H | 1 |
| 5$(CH_3)_2$N | p-$NCC_6H_4$ | $CH_3$ | $CH_3$ | $CH_3$ | H | 0 |
| 5-$CH_3$O | p-$CH_3SC_6H_4$ | n-$C_4H_9$ | $CH_3$ | $CH_3$ | $CH_3$ | 0 |
| 5-$CH_3$O | $C_6H_5$ | —$(CH_5)$— | | $CH_3$ | $C_4H_9$ | 0 |
| 5-$CH_3$O | $C_6H_5$ | $CH_3$ | $CH_3$ | $CH_3OCH_2CH_2$ | H | 1 |
| 5-$CH_3$O | 2-thienyl | $CH_3$ | $CH_3$ | $C_5H_{11}$ | H | 0 |
| 5-$CH_3$O;4$CH_3$ | 2-pyridyl | $C_2H_5$ | $C_2H_5$ | H | H | 0 |
| 5-$C_2H_5$O | 2,3-$(CH_3O)C_6H_9$ | $C_4H_3$ | $C_4H_9$ | H | H | 1 |
| 5-$(CH_3)_2$N | $C_6H_5$ | $CH_3$ | n-$C_6H_{13}$ | H | H | 1 |
| 5-$CH_3$S | p-$ClC_6H_4$ | $CH_3$ | $CH_3$ | H | H | 1 |
| 5-F | $C_6H_5$ | $CH_3$ | $CH_2CH(CH_3)_2$ | H | H | 1 |
| 5-Cl | $C_6H_5$ | $CH_3$ | $CH_3$ | H | H | 1 |
| 5-$CH_3$O | m-$CH_3C_6H_4$ | —$CH_2CH_2$—O—$CH_2CH_2$— | | H | H. | 0 |
| 5-$CH_3$O | $C_6H_5$ | —$CH_2CH_2N(CH_3)CH_2CH_2$— | | H | H | 1 |
| 5-$CH_3$O | $C_6H_5$ | cyclohexyl | H | H | H | 1 |
| 5-$CH_3$O | $C_6H_5$ | $CH_3$ | $CH_3$ | H | H | 2 |

EXAMPLE 43

(2-Phenylethynyl)phenyl-2-propanone

To a 3-necked, round bottom flask under nitrogen was added 4.0 g (18.8 mmole) of 2-bromophenyl-2-propanone in 40 ml of triethylamine, 2.5 ml (22.5 mmole) of phenylacetylene, 0.3 g (2 mole %) of bis-(triphenylphosphine) palladium dichloride and 0.14 g (4 mole %) of cuprous iodide. After refluxing for three hours another 0.5 ml (4.5 mmole) of phenylacetylene, 0.6 g (4 mole %) of bis (triphenylphosphine) palladium dichloride and 0.3 g (8 mole %) of cuprous iodide were added. Reflux was continued another 1½ hours before 1.0 ml (9.0 mmole) of phenylacetylene and 10 ml of triethylamine were added. After an additional 2½ hours at reflux the reaction was partitioned between ether and water, washed with brine, dried over MgSO$_4$ and evaporated in vacuo to yield 55 g of crude reaction product. The mixture was flash chromatographed eluting with 1:19 ethyl acetate:hexane to give 2.6 g (59%) of 2-(phenylethynyl)phenyl-2-propanone as a dark oil.

$^1$H NMR: (2.2, s, 3H), (3.9, s, 2H), (7.2–7.7, m, 4H).

EXAMPLE 44

N-Hexyl-5-methoxy-α-methyl-2-(phenylethynyl)benzeneethanmine

A solution of 4.0 g (0.015 mole) of 5-methoxy-α-methyl-2-(phenylethynyl)benzeneethanamine in 25 ml of CH$_2$Cl$_2$ was stirred and 2.0 ml (0.017 mole) of freshly distilled n-hexanal and 20 g of 5A molecular sieves were added. After four hours the sieves were removed by filtration and washed with CH$_2$Cl$_2$. The CH$_2$Cl$_2$ was evaporated in vacuo to give 5.25 g of the imine as an oil. The oil was dissolved in 25 ml of MeOH and 0.95 g (0.0151 mole) of sodium cyanoborohydride was added. Methanolic hydrogen chloride was added until the mixture was slightly acidic. The mixture was stirred for one hour. A second sample of sodium cyanoborohydride was added. The pH was adjusted to 3–5 by addition of methanolic hydrogen chloride. The mixture was stirred for two hours. Methanolic hydrogen chloride was added to lower the pH to 1. The mixture was stirred 15 minutes, the solvent was evaporated in vacuo and the residue partitioned between ether and dilute sodium hydroxide solution. The ether layer was washed with brine, dried with K$_2$CO$_3$ and the solvent evaporated in vacuo to give 4.4 g of an oil which was purified as a fumarate salt from ethanol and reconverted to the free base by partitioning between ether and sodium hydroxide solution. The ether was dried with K$_2$CO$_3$ and evaporated in vacuo to give 3.2 g (60% yield) of N-hexyl-5-methoxy-α-methyl-2-(phenylethynyl)benzeneethanamine as an oil.

$^1$H NMR(CDCl$_3$): 7.6–7.1 (m, 6H); 6.8–6.6 (m 2H); 3.8 (s, 3H); 3.4–2.2 (m, 5H), 1.8–0.7 (m, 14H).

EXAMPLE 45

N-Hexyl-5-methoxy-N,α-dimethyl-2-(phenylethynyl)benzeneethanamine (E)-2-butendioate (1:1)

A solution of 2.8 g (8.0 mmoles) of N-hexyl-5-methoxy-α-methyl-2-(phenylethynyl)benzeneethanmine, 1.6 ml (19.6 mmoles) of formalin, and 1.9 g (29.6 mmoles) of sodium cyanoborohydride was stirred for five hours at 25°. The mixture was acidified with methanolic hydrogen chloride. The solvent was evaporated in vacuo. The residue was partitioned between ether and sodium hydroxide solution. The ether layer was washed with brine, dried with K$_2$CO$_3$ and the solvent evaporated in vacuo to give 2.7 g of an oil. The fumarate salt was prepared from 2-propanol/ether and recrystallized (in two crops) from 2-propanol/methyl t-butyl ether. There was obtained 1.84 g (48% yield) of N-hexyl-5-methoxy-N,α-dimethyl-2-(phenylethynyl)benzeneethanamine (E)-2-butendioate (1:1), mp 95°–97°.

EXAMPLE 46

4,5-Dimethoxy-N,N,N-trimethyl-2-(phenylethynyl)-benzeneethanaminium iodide hydrate (2:2:1)

To a solution of 5.28 g (0.017 mole) of 4,5-dimethoxy-N,N-dimethyl-2-(phenylethynyl)benzeneethanamine in 20 ml of ethanol was added 1.43 ml (0.023 mole) of methyl iodide. The solid was collected and recrystallized successively from ethanol and methanol to afford 4.5 g of white crystalline 4,5-dimethoxy-N,N,N-trimethyl-2-(phenylethynyl)benzeneethanaminium iodide hydrate (2:2:1), mp 134°–150° C., yield 58%.

EXAMPLE 47

Ethyl 3-aminobenzenepropanoate hydrochloride

A suspension of 100 g (0.52 moles) of 3-nitrocinnamic acid in 800 ml glacial acetic acid and 100 ml of methanol was hydrogenated at 50 pounds per square inch over 2.5 g 10% palladium on carbon until four equivalents of hydrogen were absorbed. The catalyst was filtered off, the filtrates combined and the solvent was concentrated in vacuo leaving a brown glass of 3-aminobenzenepropanoic acid. To this was added 1 liter of ethanolic hydrochloric acid which was brought to reflux for five hours. The solvent was evaporated off in vacuo leaving a purple solid. Recrystallization from ethyl acetate yielded 88.0 g of ethyl 3-aminobenzenepropanoate, hydrochloride, mp 132°–135° C., (74% yield).

EXAMPLE 48

Ethyl 3-dimethylaminobenzenepropanoate

To a solution of 98.5 g (0.43 moles) of ethyl 3-aminobenzenepropanoate hydrochloride in 1500 ml of methanol and 400 ml 37% aqueous formaldehyde (4.3 moles) was added 74 g (1.16 moles) of sodium cyanoborohydride. The reaction was allowed to stir overnight under a nitrogen atmosphere. After 425 ml (5.16 moles) of propionic acid were added, the reaction mixture was refluxed for 4.5 hours. The methanol was evaporated in vacuo and the residue was brought to pH 6.8 by 25% sodium hydroxide addition. The mixture was extracted with diethyl ether which was washed with water, brine solution and dried over anhydrous potassium carbonate. The ether was evaporated in vacuo and the residue was distilled in a Kugelrohr under reduced pressure to give 74.04 g of ethyl 3-dimethylaminobenzenepropanoate, mp 94°–98° C. (oxalate), (72.1% yield).

EXAMPLE 49

3-Dimethylaminobenzenepropanoic acid hydrochloride

A solution of 69.0 g (0.31 moles) ethyl 3-dimethylaminobenzenepropanoate in 350 ml 1N sodium hydroxide was refluxed for eight hours. The pH was adjusted to the cloud point (pH 6.2) and the reaction mixture was extracted continuously with diethyl ether overnight. The ether was evaporated off in vacuo leaving an oily residue. Conversion to the hydrochloric acid salt gave 25.90 g of 3-dimethylaminobenzenepropionic acid HCl, mp 159°–162° C. (36% yield).

EXAMPLE 50

Ethyl 5-amino-2-iodobenzenepropanoate hydrochloride

To a solution of 88.0 g (0.38 moles) ethyl 3-aminobenzenepropanoate in 380 ml glacial acetic acid was added 97.3 g (0.38 moles) iodine and 96.0 g (0.57 moles) silver acetate portionwise, alternating the additions beginning with the iodine. After two hours of stirring 10 g of iodine was added and stirring was continued for an additional hour. The reaction mixture was filtered and the solid washed well with acetic acid. The filtrate was extracted with chloroform. The chloroform layer was washed with sodium bisulfite solution then evaporated in vacuo. The resulting red oil was converted to the hydrochloric acid salt giving 118.3 g of ethyl 5-amino-2-iodobenzenepropanoate hydrochloride, mp 124°–127° C. (72% yield).

EXAMPLE 51

Sodium 2-iodo-5-methylthiobenzenepropanoate

A mixture of 30 g (0.089 moles) of ethyl 2-amino-5-iodobenzenepropanoate, 30 ml water, 20 g ice and 45 ml of hydrochloric acid was stirred for one hour. The solution was cooled to 0° C. and 5.8 g (0.084 moles) of sodium nitrite in 15 ml of water were added dropwise keeping the temperature below 5° C. After stirring for one hour the reaction mixture was added to a solution of 13.5 g (0.084 moles) of potassium ethyl xanthate in 20 ml of water. This was stirred for three hours. The reaction mixture was extracted several times with diethyl ether which was evaporated in vacuo. The resulting brown oil was taken up in 95% ethanol and 18.9 g (0.336 moles) of potassium hydroxide was added. After refluxing overnight under nitrogen the reaction was cooled. Methyl iodide (10.5 ml; 0.168 moles) was added and the reaction was stirred three more hours. The ethanol was evaporated in vacuo. The residue was partitioned between 3N hydrochloric acid and diethyl ether. The ether was washed with water, brine solution and dried over Mg SO$_4$. The ether was evaporated off. Conversion to the sodium salt gave 14.3 g of sodium 2-iodo-5-methyl-thiobenzenepropanoate, mp 118°–122° C. (49% yield).

What is claimed is:

1. A method for controlling hypertension in an animal which comprises administering to the animal a therapeutically effective antihypertensive amount of an acetylene of the following formula (I):

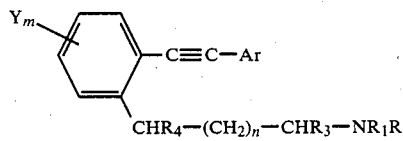

wherein

Y is independently alkyl, alkoxy, alkylthio, alkylsulfinyl, alkylsulfonyl, alkanoyloxy, alkanoylamino, amino, monoalkylamino, dialkylamino, hydroxy, halogen or cyano or methylenedioxy or ethylenedioxy at adjacent ring carbons;

m is 0, 1, 2 or 3;

Ar is phenyl or a 5- or 6-membered heterocyclic aromatic ring attached via a ring carbon to the acetylene moiety, which rings may be substituted independently by one or more of alkyl, alkoxy, alkylthio, alkylsulfinyl, alkylsulfonyl, carboxamido, halogen, fluoroalkyl or cyano;

$R_1$ and $R_2$ are independently hydrogen, alkyl, cycloalkyl or cycloalkylalkyl or $R_1$ and $R_2$ are alkyl and are joined to form a 5- to 7-membered saturated ring which ring may contain an oxygen or sulphur atom or an $NR_5$ moiety wherein $R_5$ is hydrogen or alkyl;

$R_3$ is hydrogen, alkyl or alkoxyalkyl;

$R_4$ is hydrogen or alkyl; and n is 0, 1 or 2, and the pharmaceutically acceptable acid addition salts and the quaternary ammonium compounds thereof.

2. The method of claim 1, wherein

Y is alkyl of about 1 to 6 carbons; alkoxy of about 1 to 6 carbons; alkylthio of about 1 to 6 carbons; alkylsulfinyl of about 1 to 6 carbons; alkylsulfonyl of about 1 to 6 carbons; alkanoyloxy of about 2 to 6 carbons; alkanoylamino of about 2 to 6 carbons; amino; monoalkylamino of about 1 to 6 carbons; dialkylamino of about 2 to 12 carbons; hydroxy; fluoro, chloro or bromo; cyano; or methylenedioxy or ethylenedioxy at adjacent ring carbons;

m is 0, 1, 2 or 3;

Ar is phenyl or a 5- or 6-membered heterocyclic aromatic ring attached via a ring carbon to the acetylene moiety and containing 1, 2 or 3 nitrogen, sulphur or oxygen atoms which rings may be substituted with one or more of alkyl, alkoxy, alkylthio, alkylsulfinyl or alkylsulfonyl of about 1 to 6 carbons each, carboxamido, fluoro, chloro, bromo, iodo, fluoroalkyl of about 1 to 6 carbons or cyano;

$R_1$ and $R_2$ are hydrogen; alkyl of about 1 to 8 carbons; cycloalkyl of about 3 to 6 carbons; or cycloalkylalkyl of about 4 to 7 carbons; or $R_1$ and $R_2$ are alkyl and are joined to form a 5- to 7-membered saturated ring which may contain an oxygen or sulphur atom or an $NR_5$ moiety wherein $R_5$ is hydrogen or alkyl of about 1 to 6 carbons;

$R_3$ is hydrogen; alkyl of about 1 to 6 carbons; or alkoxyalkyl of about 1 to 6 carbons in each alkyl portion;

$R_4$ is hydrogen; or alkyl of about 1 to 6 carbons; and n is 0, 1 or 2.

3. The method of claim 1, wherein said 5- or 6-membered heterocyclic ring for Ar is selected from the group consisting of thiophene, pyrrole, furan, pyrazole, imidazole, triazole, oxazole, thiazole, thiadiazole, pyridine, pyridazine, pyrimidine, pyrazine or triazine and said ring formed from $R_1$ and $R_2$ is selected from the group consisting of 1-pyrrolidinyl, 4-(alkyl of about 1 to 6 carbons)piperazinyl and 1-morpholino.

4. The method of claim 1, wherein Y is alkoxy and m is 1, 2 or 3.

5. The method of claim 1, wherein at least one of $R_3$ and $R_4$ is other than hydrogen.

6. The method of claim 1, wherein $R_1$ and $R_2$ are alkyl.

7. The method of claim 1, wherein said pharmaceutically acceptable acid addition salts are formed from acids selected from the group consisting of hydrochloric, hydrobromic, hydroiodic, sulfuric, phosphoric, fumaric, maleic, cyclohexylsulfamic, citric, lactic and methanesulfonic and said quaternary ammonium compounds are those formed with an alkylhalide or alkylsulfate.

8. The method of claim 1, wherein Y is methoxy at the position para to the acetylene moiety; m is 1; Ar is phenyl; $R_4$ is hydrogen; n is O; $R_3$ is methyl; $R_1$ is methyl; and $R_2$ is n-hexyl.

9. The method of claim 1, wherein Y is methoxy and m is 1.

* * * * *